United States Patent [19]
Howell

[11] 3,962,417
[45] June 8, 1976

[54] DENTIFRICE
[76] Inventor: Charles J. Howell, 8436 Brentwood Road, Largo, Fla. 33540
[22] Filed: Mar. 27, 1974
[21] Appl. No.: 455,266

[52] U.S. Cl. .................... 424/52; 424/44; 424/49; 424/56
[51] Int. Cl.² ........................... A61K 7/18
[58] Field of Search ............ 424/44, 49–58, 424/6

[56] References Cited
UNITED STATES PATENTS

| | | |
|---|---|---|
| 3,431,339 | 3/1969 | Gyarmathy et al. ............ 424/49 |
| 3,518,343 | 6/1970 | Welsh et al. .................... 424/44 |
| 3,629,468 | 12/1971 | Anderson ......................... 424/44 |
| 3,772,431 | 11/1973 | Mlkvy et al. .................... 424/44 |

Primary Examiner—Shep K. Rose
Attorney, Agent, or Firm—Stein, Orman & Pettis

[57] ABSTRACT

An effervescent dentifrice in chewable tablet form particularly effective in controlling *Bacillus Acidophilios* comprising a compressed homogenous mixture of an acid neutralizer, a cariespreventative, an acid, a wetting agent, and flavoring and sweetening agents. Upon crushing the dentifrice tablet in the mouth, a pleasant-tasting, effective microbicide is released.

1 Claim, No Drawings

DENTIFRICE

BACKGROUND OF THE INVENTION

1. Field of the Invention

This invention relates to an effervescent dentifrice in tablet form which when crushed in the mouth produces an effective microbicide. The tablet is particularly useful in cleaning teeth and controlling decay, and is particularly effective in neutralizing *Bacillus Acidophilios*.

2. Description of the Prior Art

Of course, various types of dentifrice preparations are well known in the art. Such preparations are generally prepared in the form of a paste intended to be applied to teeth by means of a brush. However, dental research has shown that the "sticky" nature of such preparations may actually aid in the formation of plaque on teeth surfaces unless strenuous brushing is employed.

Dentifrice preparations in powder form are also quite common in the prior art. Such powdered preparations have also proved to be unacceptable for a number of reasons. Most particularly, powdered dentifrice is somewhat difficult to use, resulting in waste, and it has a tendency to absorb water from the air resulting in caking.

In recognition of these and other shortcomings of both the paste and powder dentifrice preparations, various attempts at producing an effective dentifrice in tablet form are shown in the prior art. However, upon inspection, these tablet preparations proved to be little more than dried paste or compressed powder. Accordingly, with the possible exception of those tablets specifically intended for use on artificial dentures, a number of these prior art tablets have proved to be neither acceptable nor effective. Specifically, none of these prior art tablets demonstrate a propensity to attack and neutralize the major cause of tooth decay, *Bacillus Acidophilios*.

One such prior art composition as disclosed in U.S. Pat. No. 975,354. The composition comprises a stable mixture for producing hydrogen peroxide which is of value for dental purposes as a dentifrice. However, the composition therein described requires the presence of completely or partially dehydrated terborates. A similar product, though prepared in tablet form, is disclosed in U.S. Pat. No. 975,814. The tablet disclosed in that patent appears to depend entirely for its effectiveness on the presence of peroxide of hydrogen. Yet another form of dentifrice relying on the reaction of sodium terborate with saliva to form hydrogen peroxide is disclosed in U.S. Pat. No. 1,516,398.

Finally, U.S. Pat. Nos. 3,518,343 and 3,577,490, both relate to an effervescent tablet and a process for making the same. The tablet disclosed in these two patents is intended to be dissolved to form a solution useful as a mouthwash. Additionally, the disclosures of both these patents indicate that the utility and the stability of the tablet are directly linked to the tableting lubricant claimed therein. Of course it seems apparent that the critical nature of the tableting lubricant and the complexity of its manufacture necessarily increase the cost of the tablet.

Accordingly, it is obvious that there is a need in the dentifrice industry for a convenient, effective dentifrice in tablet form. Such a dentifrice should, most importantly, neutralize the *Bacillus Acidophilios*, which modern dental research has found to be the principal bacterium causing tooth decay. The dentifrice should be pleasant tasting, and it should be capable of being used anywhere by placing it directly in the mouth. Since the dentifrice is to be prepared in tablet form, it must be of sufficient hardness to retain its tablet form, but it must be soft enough to be crushed even by a child. Finally, such a dentifrice tablet must be economical, both to the manufacturer and to the purchaser.

SUMMARY OF THE INVENTION

The present invention relates to a dentifrice in tablet form which is easy to use, pleasant tasting, and particularly effective in neutralizing the major cause of tooth decay. The tablet of the present invention is prepared by first making a homogeneous mixture of the several constituents. Once the homogeneous mixture of the constitutents is prepared, tablets of preferably five grain size are prepared. Of course, the tablet must be of sufficient hardness to retain its shape in packaging and shipping, but it must be soft enough so that even a child may crush it.

To accomplish its primary function of neutralizing the *Bacillus Acidophilios*, the tablet comprises approximately 70–75% by weight, acid neutralizer and approximately 17–20%, by weight, acid. The initial reaction of the acid neutralizer and the acid serves to create an effervescent action in the mouth. The resulting basic solution then neutralizes the acidic *Bacillus Acidophilios*. In order to further protect the teeth of the user it has been found desirable to add approximately 1.0–1.2%, by weight, caries-preventative. It has further been found desirable to add flavoring agents, a breath deodorant and a wetting agent to the composition of the tablet, in order to provide a pleasant-tasting product. These ingredients total approximately 4.0–5.4%, by weight. Finally, approximately 1.5–2.0%, by weight, of the five grain tablet comprises an excipient in order to provide for a tabletable product.

By virtue of the composition of the present invention, an extremely effective, pleasant-tasting, convenient dentifrice is provided. As will be set forth more fully hereinafter, it should also be noted that none of the ingredients of the dentifrice of this invention are abrasive; all are completely soluble. Therefore, there is no danger of wearing away the enamel of the teeth when using it. It should also be noted that at present many dentists stress strenuous brushing as the best means of removing plaque from the teeth, which is aided in its formation by the use of a toothpaste which is inherently sticky. Accordingly, it should be noted that not only does the effervescent action of the present dentifrice assist in the removal of plaque, but also the very nature of the composition of this invention eliminates the stickiness normally associated with current toothpastes which may aid in plaque formation.

This invention accordingly comprises an article of manufacture possessing the features, properties and the relation of elements which will be exemplified in the article hereinafter described, and the scope of the invention will be indicated in the claims.

DETAILED DESCRIPTION

This invention relates to an effervescent dentifrice in tablet form intended for oral use for the prevention of tooth decay. In order to more clearly define the composition of this invention, the example which follows is given with regard to a preferred embodiment for the production of a dentifrice in tablet form.

EXAMPLE I

The ingredients of the dentifrice tablet were dry-mixed in the following proportions. (All percentages are given by weight.)

| Substance | Percent By Weight |
|---|---|
| Saccharin | 0.317 |
| Sodium Lauryl Sulphate | 1.453 |
| Chlorophyllin | 0.279 |
| Magnesium Carbonate | 11.173 |
| Citric Acid | 18.622 |
| Calcium Carbonate | 21.229 |
| Sodium Bicarbonate | 40.223 |
| Sealva Floral Mint | 0.931 |
| Sealva Peppermint | 2.793 |
| Magnesium Stearate | 0.931 |
| Acacia Powder | 0.931 |
| Stannous Fluoride | 1.117 |

After these ingredients were thoroughly mixed, the composition was then formed into tablets of approximately 5 grains each by a standard rotary tableting machine.

The tablets obtained thereby were of sufficient hardness to retain their shape in packaging operations, but were sufficiently soft to be crushed easily in the mouth.

One of the tablets was placed in a small quantity of water, and an extremely effervescent reaction was observed. The resulting solution showed that all the ingredients of the tablet had been dissolved, and the solution was found to be particularly effective in neutralizing the acidic *Bacillus Acidophilios*.

EXAMPLE II

Another of the dentifrice tablets prepared in accord with the formula of Example I was selected for use in cleansing teeth. The tablet was placed in the mouth of the user and crushed by him. A pleasant, tingling effervescent reaction was immediately noted. The user then proceeded to brush and rinse in the normal fashion. The user noted that the tablet was pleasant tasting, and that it left his mouth and teeth feeling clean. He further noted that no abrasive particles were detected during use of the tablet.

It should also be noted that by virtue of the composition of the present tablet, it is also suitable for use in locations where potable water may not be available. That is, while brushing and rinsing when using the tablet are preferred, these operations are not essential to the bacteria-killing action of the tablet. Furthermore, because of its effervescent character, use even without brushing will significantly remove food particles, resulting in a corresponding reduction in the formation of plaque.

It will thus be seen that the objects made apparent from the preceding description are efficiently attained, and since certain changes may be made in the above composition without departing from the scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described, what is claimed is:

1. A method for cleansing teeth which comprises:
   a. placing an effervescent dentifrice tablet wherein the constituent ingredients consist of 0.317% saccharin, 0.931% floral mint, 2.793% peppermint, 0.279% sodium copper chlorophyllin, 1.453% sodium lauryl sulfate, 11.173% magnesium carbonate, 21.229% calcium carbonate, 40.223% sodium bicarbonate, 18.622% citric acid, 1.117% stannous flouride, 0.913% magnesium sterate and 0.931% acacia powder, all percents by weight, directly into the mouth containing or having present a principal bacterium causing tooth decay acids, *Bacillus Acidophilios;*
   b. orienting said tablet between the teeth;
   c. crushing said tablet between the teeth;
   d. completely dissolving said ingredients into a basic solution utilizing moisture in the mouth;
   e. circulating the formed basic solution throughout the mouth and about the teeth therein;
   f. brushing the teeth with said formed solution utilizing a brushing instrument, thereby neutralizing the acidic *Bacillus Acidophilios;*
   g. expectorating said formed solution subsequent to said brushing; and
   h. rinsing the mouth so as to remove remnants of said formed solution.

* * * * *